United States Patent [19]
Liu

[11] Patent Number: 5,899,887
[45] Date of Patent: May 4, 1999

[54] SAFETY SYRINGE WITH RETRACTABLE STANDARD NEEDLE

[76] Inventor: Wen-Neng Liu, 19508 Nicholas Ave, Cerritos, LA., Calif. 90701

[21] Appl. No.: 09/089,259

[22] Filed: Jun. 3, 1998

Related U.S. Application Data

[63] Continuation-in-part of application No. 08/998,495, Dec. 26, 1997.

[30] Foreign Application Priority Data

Apr. 10, 1998 [TW] Taiwan ................... 87105506

[51] Int. Cl.⁶ ..................................................... A61M 5/00
[52] U.S. Cl. ........................... 604/195; 604/218; 604/110
[58] Field of Search ...................................... 604/195, 110, 604/187, 263, 218; 128/919

[56] References Cited

U.S. PATENT DOCUMENTS

| | | | |
|---|---|---|---|
| 5,393,301 | 2/1995 | Goldberg | 604/110 |
| 5,395,346 | 3/1995 | Maggioni | 604/195 |
| 5,401,246 | 3/1995 | Mazur et al. | 604/110 |
| 5,405,327 | 4/1995 | Chen | 604/195 X |
| 5,693,023 | 12/1997 | Adams | 604/195 |

*Primary Examiner*—John D. Yasko
*Attorney, Agent, or Firm*—Rosenberg, Klein & Bilker

[57] ABSTRACT

A safety syringe with retratable standard needle, including a syringe barrel, a plunger and an injection needle. A commonly used standard needle holder is replaceably connected with a second needle holder, whereby a user can conveniently replace the injection needle with another type of injection needle as necessary. A first needle pulling member is formed on the needle holder or the plunger, having at least one rotatable click. A second needle pulling member is formed on the plunger or the needle holder, having a detent. When the piston of the plunger is pushed to the bottom, the detent is easily and firmly engaged and hooked with the click. Thereafter, the injection needle and the needle holder can be together pulled into the barrel so as to ensure that the injection needle will not impale medical personnel or other persons.

7 Claims, 10 Drawing Sheets

SAFETY SYRINGE WITH RETRACTABLE STANDARD NEEDLE

CROSS-REFERENCE TO RELATED APPLICATION

This application ia a Continuation-in-Part Application of U.S. patent application Ser. No. 08/998,495, entitled "A Retractable and Destructible Safety Syringe", filed on Dec. 26, 1997, now pending.

BACKGROUND OF THE INVENTION

1. Field of the Invention

The present invention relates to a safety syringe in which the needle is retractable after injection.

2. Description of the Prior Art

Various types of disposable syringes are widely used nowadays. After discarded, large amount of such syringes result in problem of pollution of environment. The used syringes often impale medical personnel and infect the personnel with viruses or bacteria carried by the patients. Especially, in case the medical personnel are infected with AIDS virus, the personnel may die innocently.

In order to solve these problems, various types of retractable syringes have been developed. For example, a spring is installed between the syringe barrel and the piston for pulling the needle back into the barrel after injection. However, due to the property of the liquid medicine, the material of the spring is strictly limited. Therefore, the structure of such syringe is complicated and the manufacturing cost is very high. Various types of safety syringes free from the springs have been also developed. In such syringe, a latch member is disposed at the bottom of the barrel, whereby when the plunger is pushed to the bottom of the barrel, the latch member latches the plunger with the needle. Therefore, when the plunger is pulled back, the needle is retracted into the barrel along with the plunger so as to avoid impalement of the medical personnel or other persons.

As of the present time, all the existing safety syringes must be used with specifically designed and manufactured injection needles which cannot be replaced. Therefore, the suppliers must manufacture various kinds of safety syringes and injection needles.

SUMMARY OF THE INVENTION

In order to solve the above problems, it is an object of the present invention to provide a safety syringe with retratable standard needle. The safety syringe employs a commonly used standard needle holder for a user to conveniently replace the injection needle with another type of injection needle as necessary.

It is a further object of the present invention to provide the above safety syringe in which the plunger can be easily aligned with the injection needle and latched therewith. Also, the plunger can be firmly engaged with the injection needle, so that the injection needle can be reliably pulled into the barrel to avoid impalement of medical personnel.

According to the above objects, the safety syringe of the present invention includes: a syringe barrel having a first end and a second end, the syringe barrel being formed with an internal barrel chamber, the first end of the barrel being disposed with a needle socket defining a needle holder cavity, an annular shoulder section being formed between the barrel chamber and the needle holder cavity; a plunger having a first and a second ends, the first end being disposed with a piston and fitted into the barrel, the plunger having a first axis; a first needle holder having a first and a second ends, the second end of the first needle holder having a first fitting section; an injection needle inserted into the first end of the first needle holder; a second needle holder having a first end, a second end, a second fitting section and a plug section, the second fitting section being disposed at the first end and detachably connected with the first fitting section of the first needle holder, the plug section being disposed at the second end and fitted in the needle holder cavity of the needle socket, the second needle holder having a second axis, the second needle holder being formed with a through hole coaxial with the second axis for guiding a liquid medicine to flow through the through hole toward the injection needle or flow from the injection needle through the through hole into the barrel; and a needle pulling mechanism including: a first needle pulling member having a first end and a second end, the first end being integrally connected with one of the first end of the plunger and the second end of the second needle holder, the first needle pulling member having at least one click each having a first end and a second end, the first end being rotatably connected with the second end of the first needle pulling member, a distance between the first end of the click and either of the first axis and second axis being defined as a first distance, the second end of the click extending to the first end of the first needle pulling member, a distance between the second end of the click in a free state and either of the first axis and second axis being defined as a second distance which is less than the first distance, a distance between the second end of the click and the first end of the first needle pulling member being defined as a third distance, a distance between the first end of the click and the first end of the first needle pulling member being defined as a fourth distance which is larger than the third distance, whereby the click is formed as a ratchet; and a second needle pulling member having a first end and a second ends, the first end being connected with the other of the first end of the plunger and the second end of the second needle holder, the first end of the second needle pulling member being formed as a stem and the second end of the second needle pulling member being formed as a detent having a hook section, the hook section being formed with a radially extending hook face, when the first end of the plunger is pushed to the first end of the barrel, the hook section of the detent stretching open and sliding over the second end of the click, when the plunger is pulled from the first end of the barrel to the second end thereof, the hook face of the hook section of the detent abutting against the second end of the click with the stem tightly clamped by the second end of the click, whereby the first needle holder, the second needle holder and the injection needle can be together pulled into the barrel.

The safety syringe further includes at least two radially arranged clicks. The first needle holder is a commonly used standard needle holder and the first fitting section thereof is formed with a truncated conic cavity.

The second fitting section is formed as a truncated cone for detachably fitting into the truncated conic cavity of the first fitting section. The safety syringe further includes a leakproof structure including at least one sealing ring integrally formed on one of the wall of the needle holder cavity and the outer wall of the plug section of the second needle holder, the sealing ring sealedly contacting with the other of the wall of the needle holder cavity and the outer wall of the plug section of the second needle holder.

The safety syringe further includes a leakproof structure including at least one first sealing ring and at least one second sealing ring, the first sealing ring being integrally formed on one of the wall of the needle holder cavity and the outer wall of the plug section of the second needle holder, the first sealing ring sealedly contacting with the other of the wall of the needle holder cavity and the outer wall of the plug section of the second needle holder, the second sealing ring being integrally formed on the other of the wall of the needle holder cavity and the outer wall of the plug section of the second needle holder, the second sealing ring sealedly contacting with said one of the wall of the needle holder cavity and the outer wall of the plug section of the second needle holder.

One of the first and second sealing rings is adjacent to the other of the first and second sealing rings.

The present invention can be best understood through the following description and accompanying drawings, wherein:

DETAILED DESCRIPTION OF THE PREFERRED EMBODIMENTS

Please refer to FIGS. 1 to 8. The safety syringe 20 of the present invention includes a syringe barrel 21, a plunger 22, a first needle holder 23, a second needle holder 69, an injection needle 24. The syringe barrel 21 has a first and a second ends 28, 29. The syringe barrel 21 is formed with an internal barrel chamber 27. The first end 28 of the syringe barrel 21 is disposed with a needle socket 30 defining a needle holder cavity 31. An annular shoulder section 33 is formed between the barrel chamber 27 and the needle holder cavity 31. The plunger 22 has a first and a second ends 34, 35. The first end 34 is disposed with a piston 36 and fitted into the barrel 21. The plunger 22 has a first axis 47.

The first needle holder 23 has a first and a second ends 37, 38. The second end 38 of the first needle holder 23 has a first fitting section 70. The injection needle 24 is inserted into the first end 37 of the first needle holder 23. The second needle holder 69 has a first end 71, a second end 72, a second fitting section 73 and a plug section 74. The second fitting section 73 is disposed at the first end 71 and is detachably connected with the first fitting section 70 of the first needle holder 23. The plug section 74 is disposed at the second end 72 and fitted in the needle holder cavity 31 of the needle socket 30. The second needle holder 69 has a second axis 48. The second needle holder 48 is formed with a through hole 75 coaxial with the second axis 48 for guiding a liquid medicine to flow from the barrel 21 through the through hole 75 toward the injection needle 24 or flow from the injection needle 24 through the through hole 75 into the barrel 21.

Figure 1:
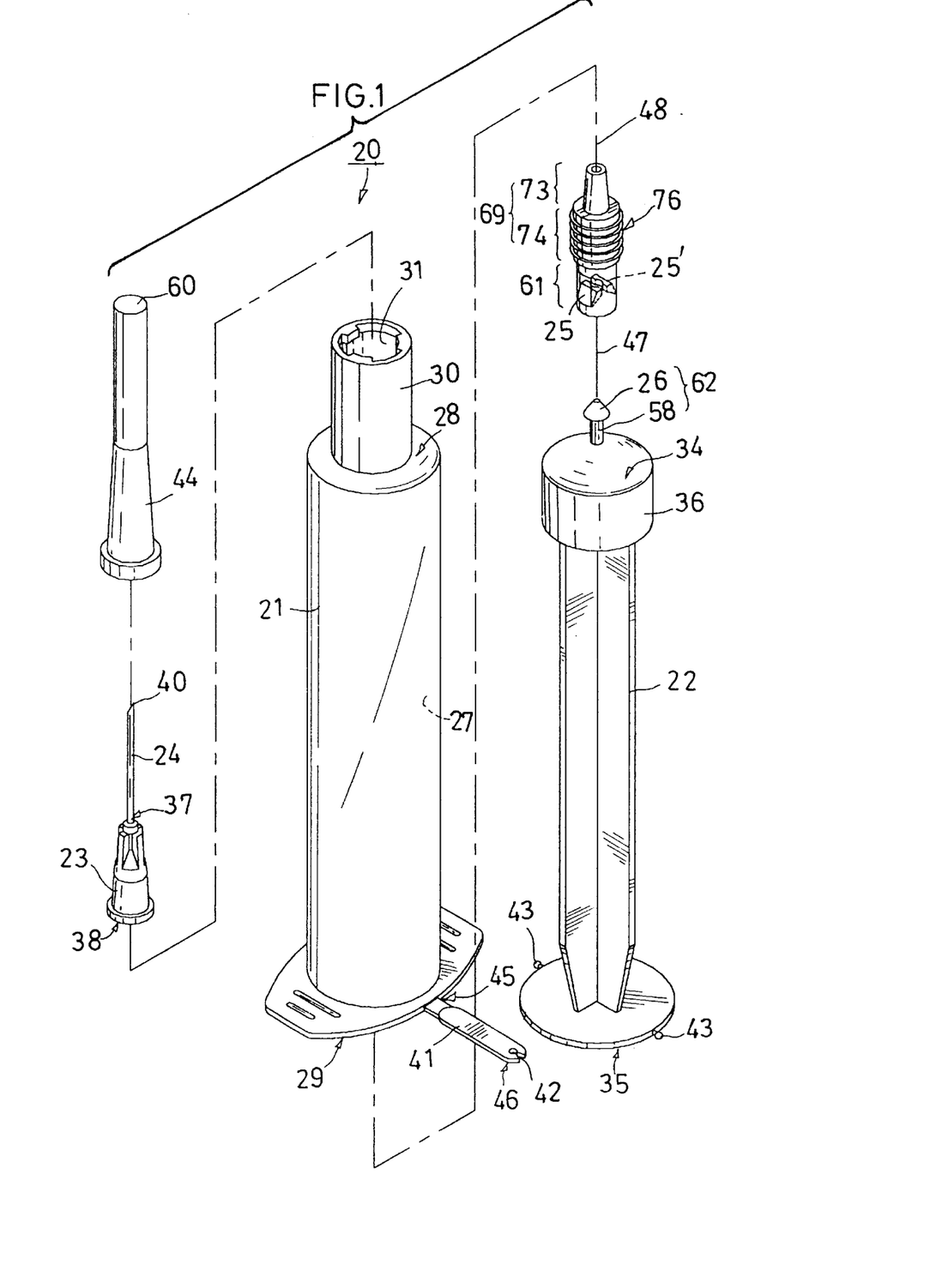
FIG. 1 is a perspective exploded view of a first embodiment of the present invention.
Figure 2:
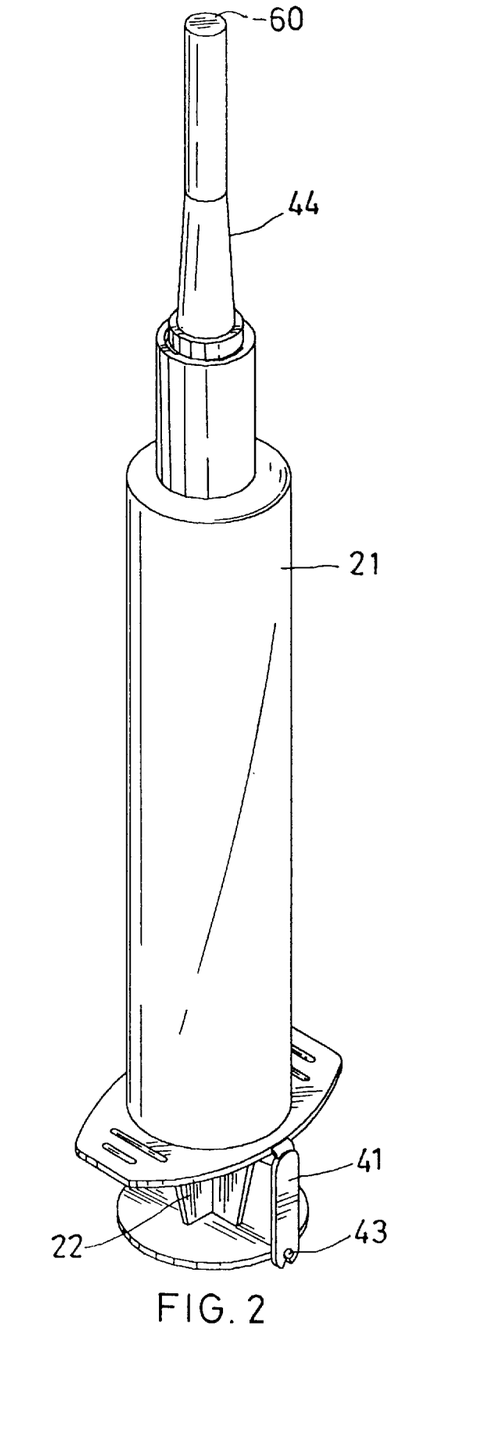
FIG. 2 is a perspective assembled view of the first embodiment of FIG. 1.
Figure 3:
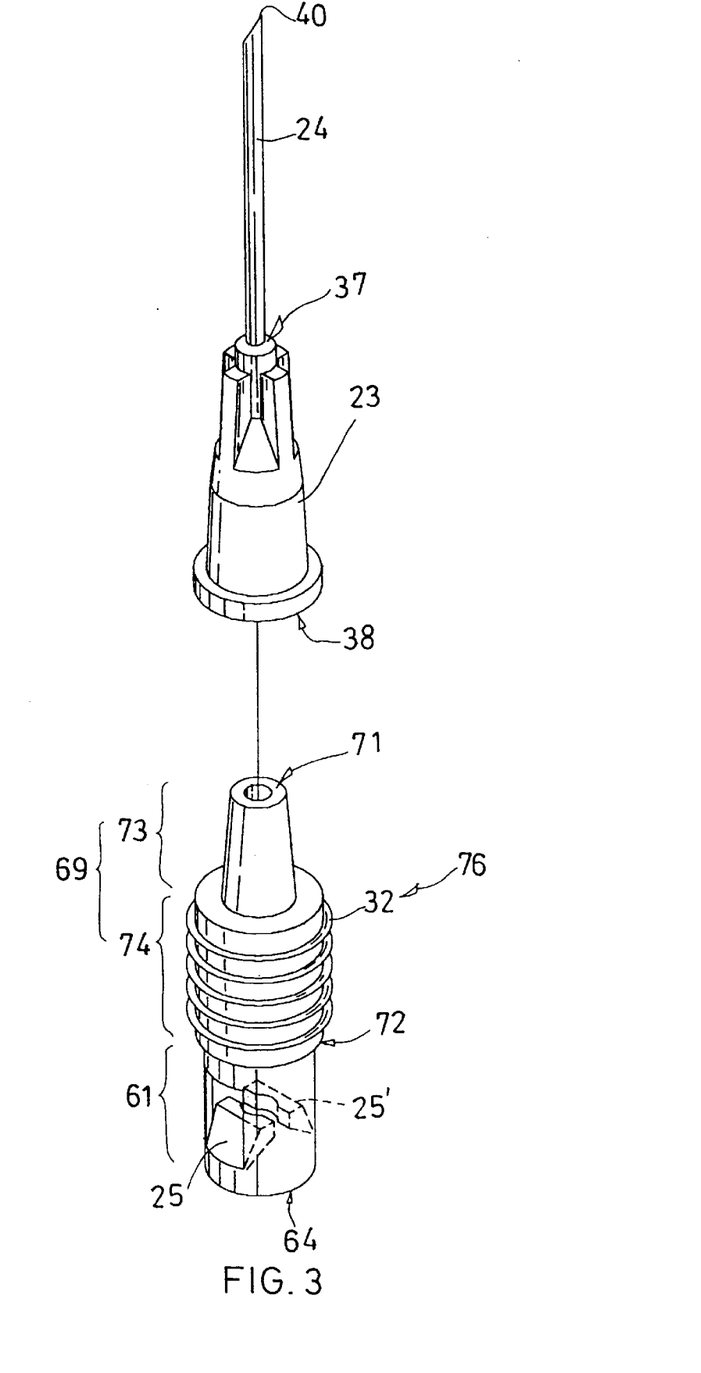
FIG. 3 is a top perspective exploded view of the injection needle and needle holders of the first embodiment of the present invention.
Figure 4:
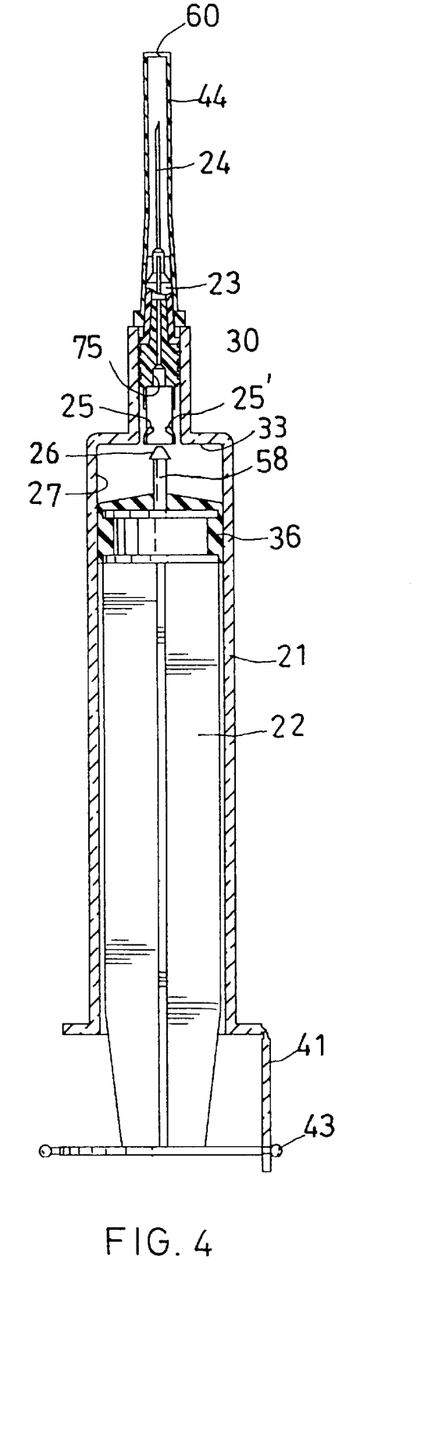
FIG. 4 is a longitudinally sectional view of the first embodiment, showing that the liquid medicine is about to be sucked into the barrel.

The first needle holder 23 of the present invention is a common standard needle holder. The first fitting section 70 is formed with a truncated conic cavity, while the second fitting section 73 is formed as a truncated cone for detachably fitting into the truncated conic cavity of the first fitting section 70.

After the second needle holder 69 is plugged into the needle holder cavity 31, the second fitting section 73 of the second needle holder 69 extends out of the needle socket 30. Under such circumstance, the second end 38 of the first needle holder 23 can be extended into the needle holder cavity 31 of the needle socket 30 to tightly fit the first fitting section 70 into the second fitting section 73 of the second needle holder 69. When it is desired to replace the needle with another type of injection needle, the injection needle 24 together with the first needle holder 23 is disconnected from the second fitting section 73 of the second needle holder 69. The truncated conic cavity of the first fitting section 70 has such an inclination angle of about 10 degrees that the first needle holder 23 can be pulled into the barrel 21 along with the second needle holder 69 without detachment. In addition, the fitting force between the second needle holder 69 and the wall of the needle holder cavity 31 is much greater than the connecting force between the first and second fitting sections 70, 73. Therefore, when replacing the needle, the first needle holder 23 can be pulled out without changing the position of the second needle holder 69 in the needle holder cavity 31. In addition, a needle sheath 44 is fitted around the first needle holder 23 to prevent the injection needle 24 from impaling the patient or medical personnel prior to injection. Accordingly, a user can freely replace the injection needle with another type of injection needle as necessary. This cannot be achieved by all the existing safety syringes.

Please refer to FIGS. 1, 3, 8 and 9. The present invention further includes a needle pulling mechanism including a first and a second needle pulling members 61, 62. The first needle pulling member 61 has a first and a second ends 63, 64. The first end 63 is connected with one of the first end 34 of the plunger 22 and the second end 72 of the second needle holder 69. The first needle pulling member 61 has two clicks 25, 25' (at least one click 25 in this invention) each having a first end 49, 49' and a second end 50, 50'. The first end 49, 49' is rotatably connected with the second end 64 of the first needle pulling member 61. The distance between the first end 49, 49' of the click 25, 25' and either of the first axis 47 and second axis 48 is defined as a first distance 51. The second end 50, 50' of the click 25, 25' extends to the first end 63 of the first needle pulling member 61. The distance between the second end 50, 50' of the click 25, 25' in a free state and either of the first axis 47 and second axis 48 is defined as a second distance 52 which is less than the first distance 51. The distance between the second end 50, 50' of the click 25, 25' and the first end 63 of the first needle pulling member 61 is defined as a third distance 67. The distance between the first end 49, 49' of the click 25, 25' and the first end 63 of the first needle pulling member 61 is defined as a fourth distance 68 which is larger than the third distance 67, whereby the click 25, 25' is formed as a ratchet.

The second needle pulling member 62 has a first and a second ends 65, 66. The first end 65 is connected with the other of the first end 34 of the plunger 22 and the second end 72 of the second needle holder 69. The first end 65 of the second needle pulling member 62 is formed as a stem 58 and the second end 66 of the second needle pulling member 62 is formed as a detent 26 having a hook section 55. The hook section 55 is formed with a radially extending hook face 56. When the first end 34 of the plunger 22 is pushed to the first end 28 of the barrel 21, the hook section 55 of the detent 26 stretches open and slides over the second end 59, 50' of the click 25, 25'. When the plunger 22 is pulled from the first end 28 of the barrel 21 to the second end 29 thereof, the hook face 56 of the hook section 55 of the detent 26 abuts against the second end 50, 50' of the click 25, 25' with the stem 58 tightly clamped by the second end 50, 50' of the click 25, 25'. Therefore, the first needle holder 23, the second needle holder 69 and the injection needle 24 are together pulled into the barrel 21.

Referring to FIGS. 1 and 3, the safety syringe 20 of the present invention can further include at least two radially arranged clicks 25, 25' as necessary.

The present invention further includes a leakproof structure 76 including at least one sealing ring 32 or 39 integrally formed on one of the wall of the needle holder cavity 31 and the outer wall of the plug section 74 of the second needle holder 69. The sealing ring 32 or 39 sealedly contacts with the other of the wall of the needle holder cavity 31 and the outer wall of the plug section 74 of the second needle holder 74.

The leakproof structure 76 further includes at least one first sealing ring 32 and at least one second sealing ring 39. The first sealing ring 32 is integrally formed on one of the wall of the needle holder cavity 31 and the outer wall of the plug section 74 of the second needle holder 69. The first sealing ring 32 sealedly contacts with the other of the wall of the needle holder cavity 31 and the outer wall of the plug section 74 of the second needle holder 69. The second sealing ring 39 is integrally formed on the other of the wall of the needle holder cavity 31 and the outer wall of the plug section 74 of the second needle holder 69. The second sealing ring 39 sealedly contacts with said one of the wall of the needle holder cavity 31 and the outer wall of the plug section 74 of the second needle holder 69. One of the first and second sealing rings 32, 39 is adjacent to the other of the first and second sealing rings 32, 39.

Please refer to FIGS. 1, 2, 4 and 5. The safety syringe 20 of the present invention further includes an ensurance latch plate 41, a first latch section 42 and a second latch section 43. The latch plate 41 has a first end 45 and a second end 46. The first end 45 is connected with the second end 29 of the barrel 21. The first latch section 42 is disposed at the second end 46 of the latch plate 41, while the second latch section 43 is disposed at the second end 35 of the plunger 22. The second latch section 43 can be latched with the first latch section 42 to locate the detent 26 near the click 25, 25' without latching with each other by mis-operation.

Prior to use, as shown in FIGS. 1 to 4, the injection needle 24 is installed in the needle holder cavity 31 of the needle socket 30. By means of the sealing ring 39 of the second needle holder 69 and the sealing ring 32 of the inner wall of the needle holder cavity 31, the second needle holder 69 is sealedly and firmly engaged with the needle holder cavity 31. Then the needle sheath 44 is fitted around the injection needle 24 and the plunger 22 and piston 36 are plugged into the barrel chamber 27 of the syringe barrel 21. In addition, the first latch section 42 of the ensurance latch plate 41 is latched with the second latch section 43 of the second end 35 of the plunger 22, whereby the detent 26 is kept adjacent to the click 25 but spaced therefrom so that the detent 26 and the click 25 are prevented from latching with each other due to mis-operation.

Figure 5:
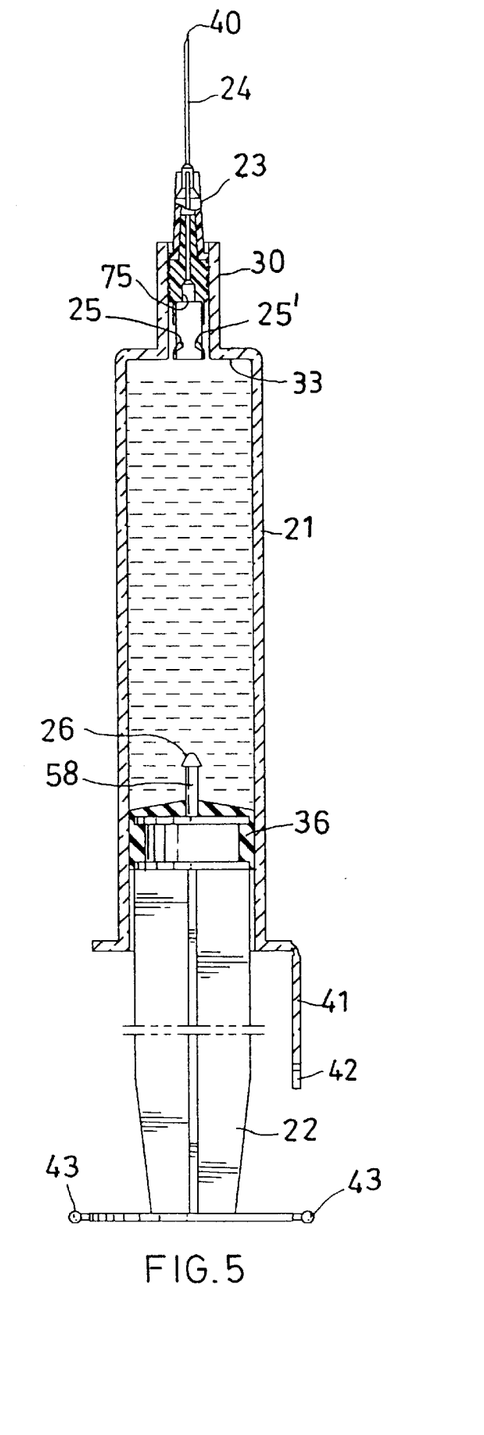
FIG. 5 is a longitudinally sectional view according to FIG. 4, showing that the liquid medicine is sucked into the barrel.
Figure 6:
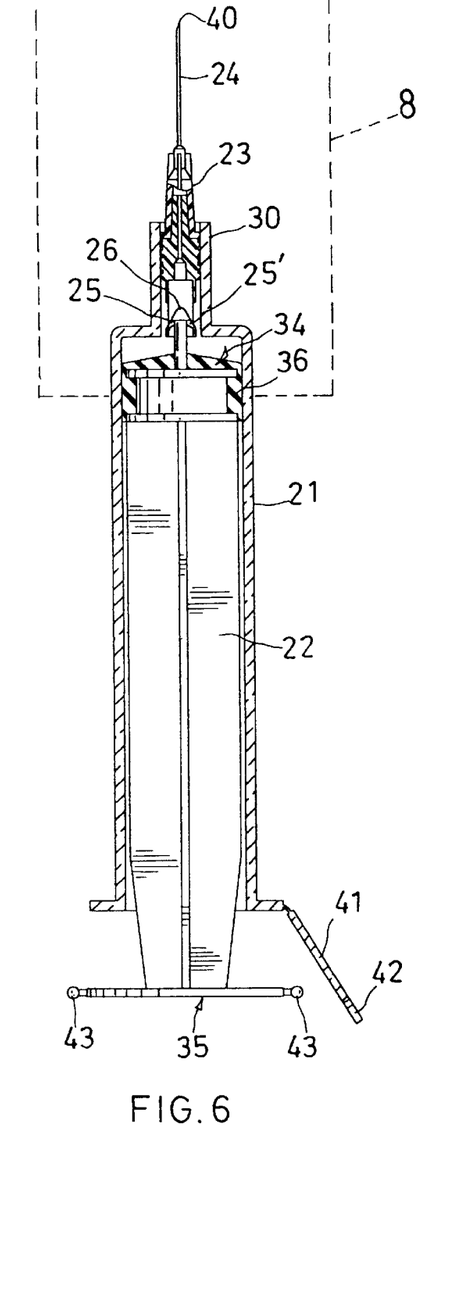
FIG. 6 is a longitudinally sectional view showing that the liquid medicine is completely injected and the detent of the plunger is hooked with the click of the needle holder of the first embodiment.
Figure 8:
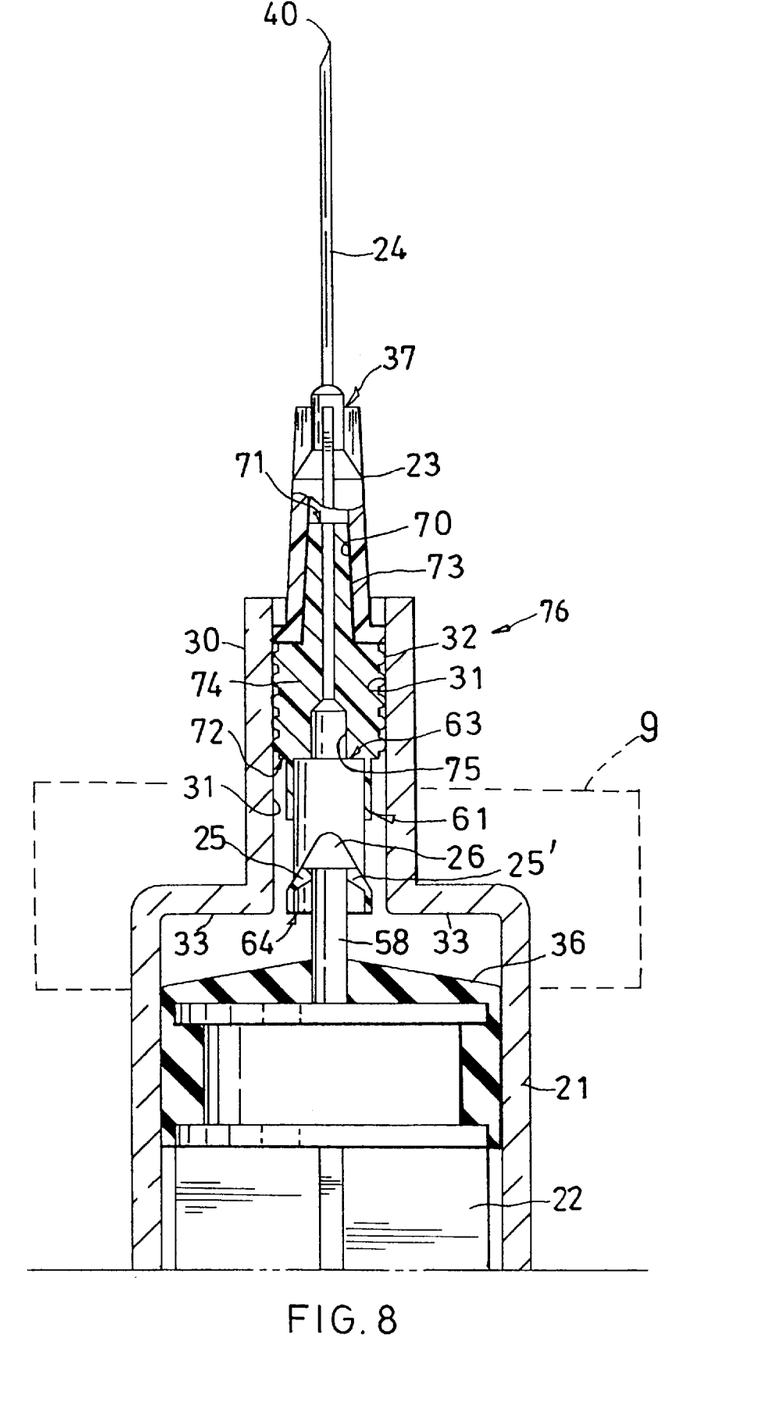
FIG. 8 is an enlarged view of area 8 defined by phantom line of FIG. 6, showing that the plunger is pulled downward and the detent is clamped by two clicks.
Figure 9:
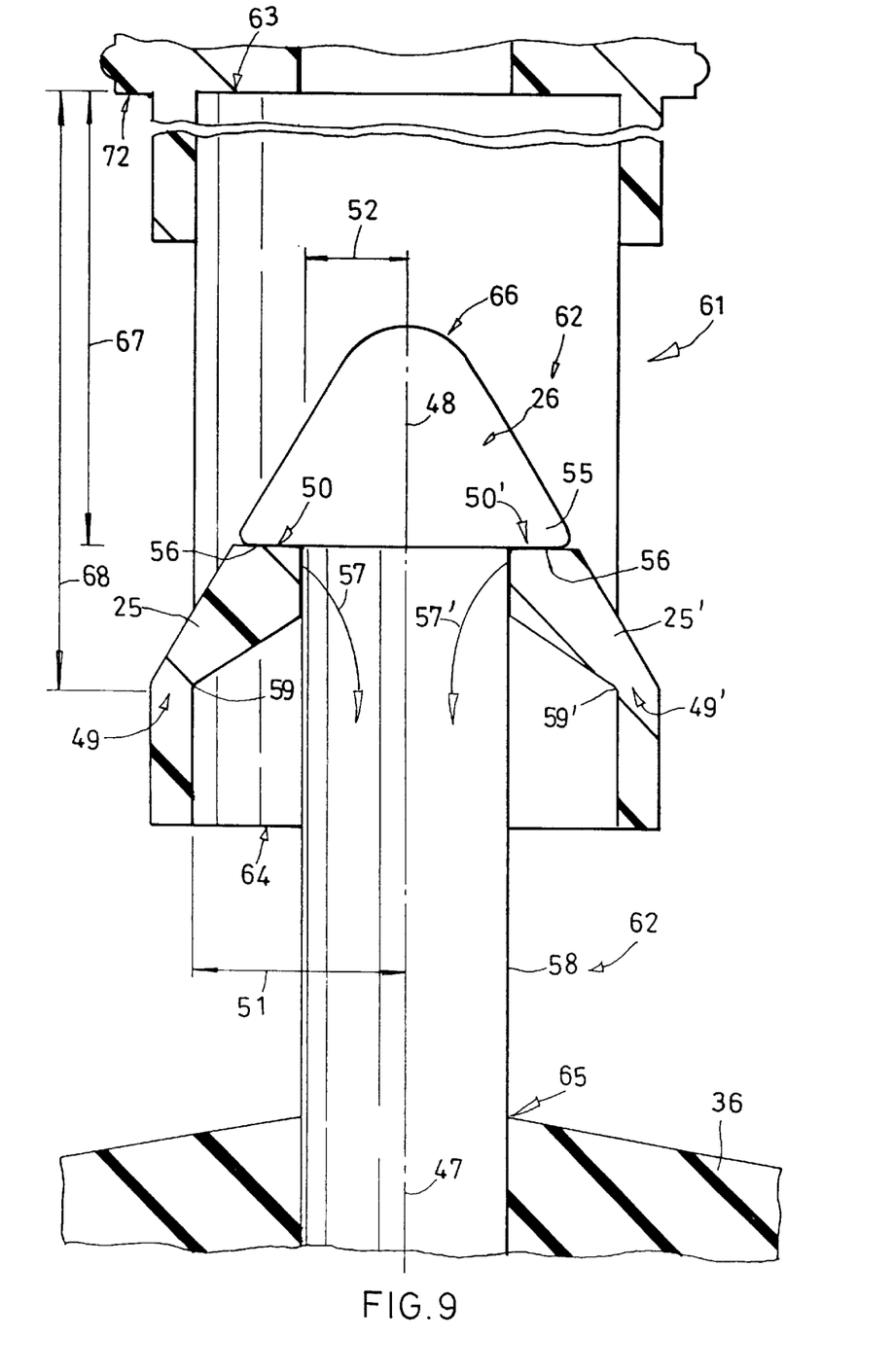
FIG. 9 is an enlarged view of area 9 defined by phantom line of FIG. 8.
Figure 10:
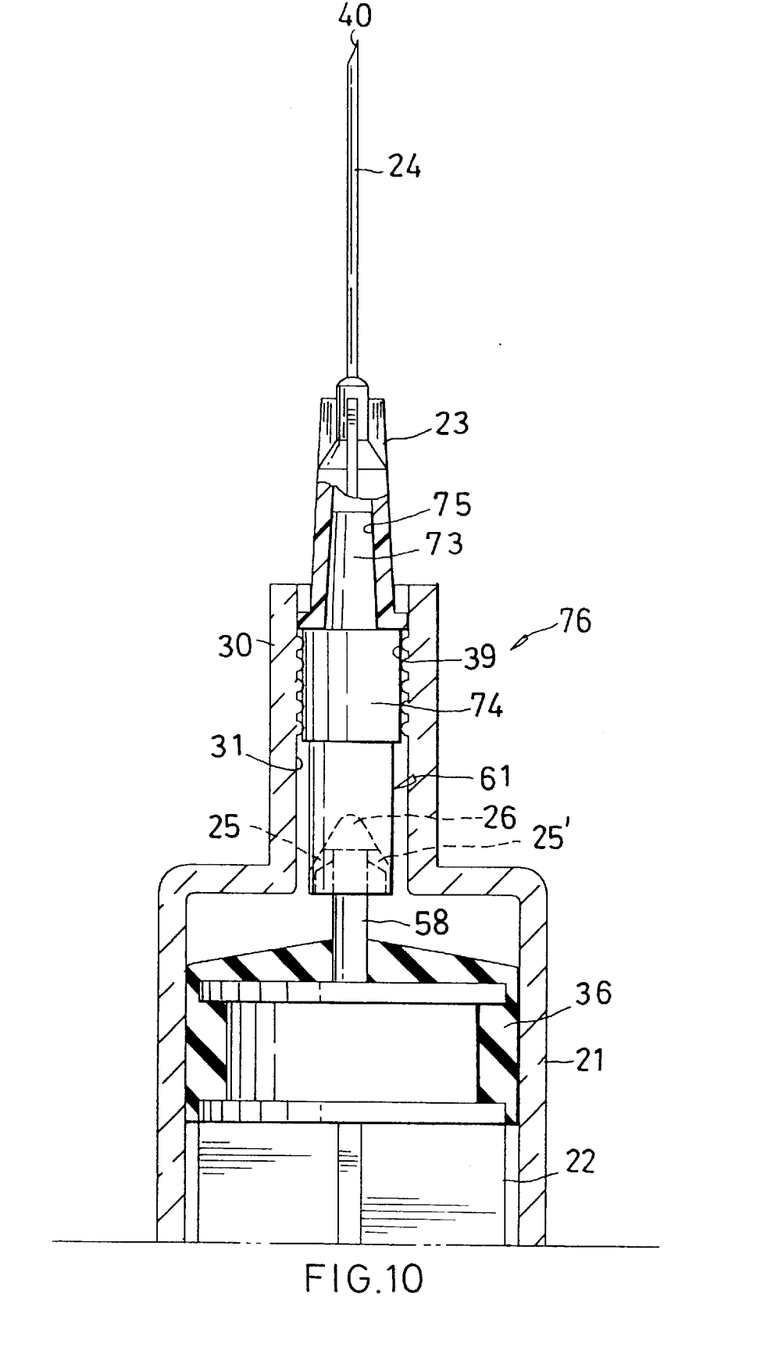
FIG. 10 is a partially sectional view of a second embodiment of the present invention.
Figure 11:
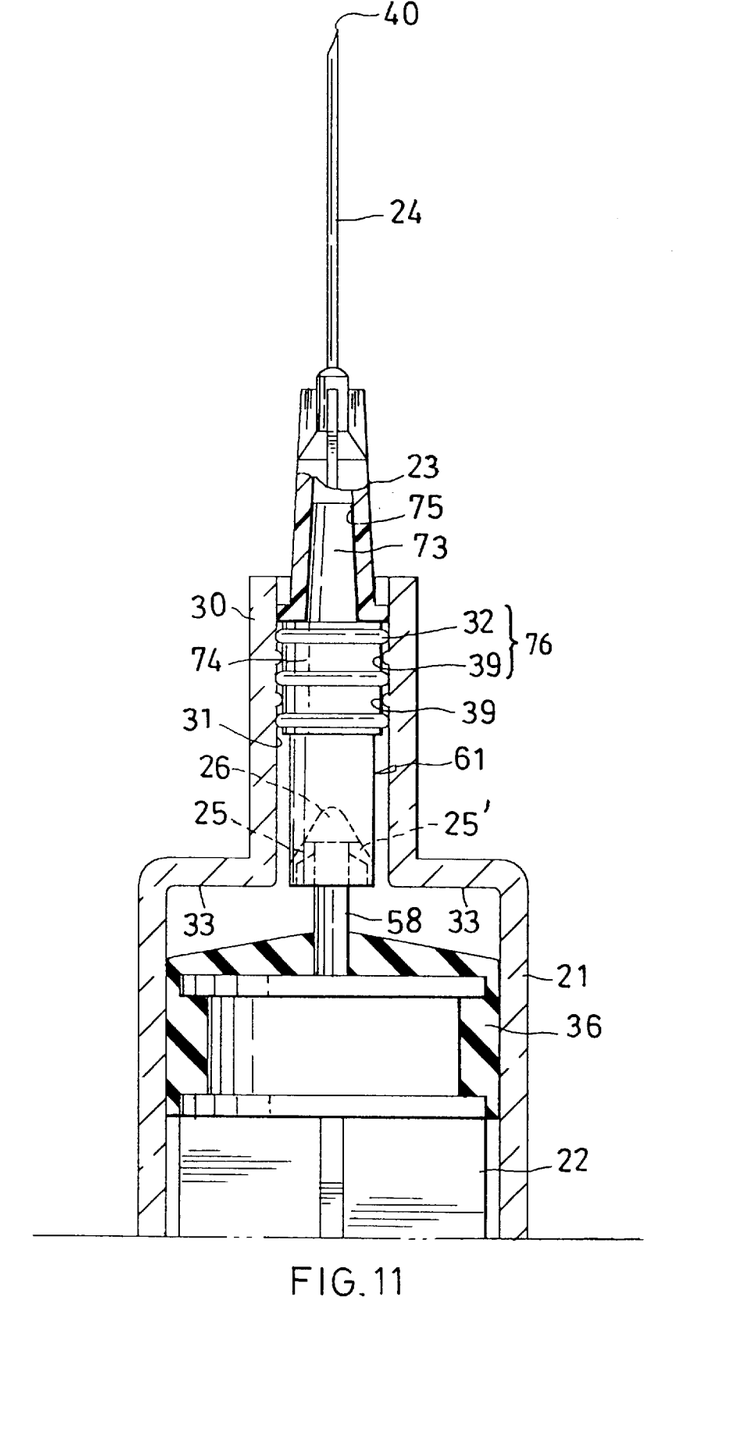
FIG. 11 is a partially sectional view of a third embodiment of the present invention.

In injection, the injection needle 24 is first thrusted into the liquid medicine and then the ensurance latch plate 41 is unlatched to pull the plunger 22 outward for sucking the liquid medicine into the barrel 21 (as shown in FIG. 5). Then the injection needle 24 is faced upward and the plunger 22 is slightly pushed upward for discharging the air in upper portion of the barrel 21 out of the tip 40 of the injection needle 24. Then the injection can be performed. After the injection is completed, as shown in FIGS. 6 to 9, the plunger 22 is pushed to the bottom and the detent 26 easily pushes open the clicks 25, 25' to hook therewith. The second distance 52 is less than the first distance 51 and the third distance 67 is less than the fourth distance 68, so that, as shown in FIGS. 8 and 9, when pulling back the plunger 22, the opposite clicks 25, 25' are depressed by the hook face 56 of the detent 26 to rotate about the bending sections 59, 59' in a direction shown by arrows 57, 57'. Therefore, the opposite clicks 25, 25' firmly clamp the stem of the detent 26. The greater the downward pulling force of the plunger 22 is, the greater the clamping force is. Therefore, the detent 26 is reliably firmly engaged with the clicks 25, 25' as shown in FIGS. 8 and 9.

Figure 7:
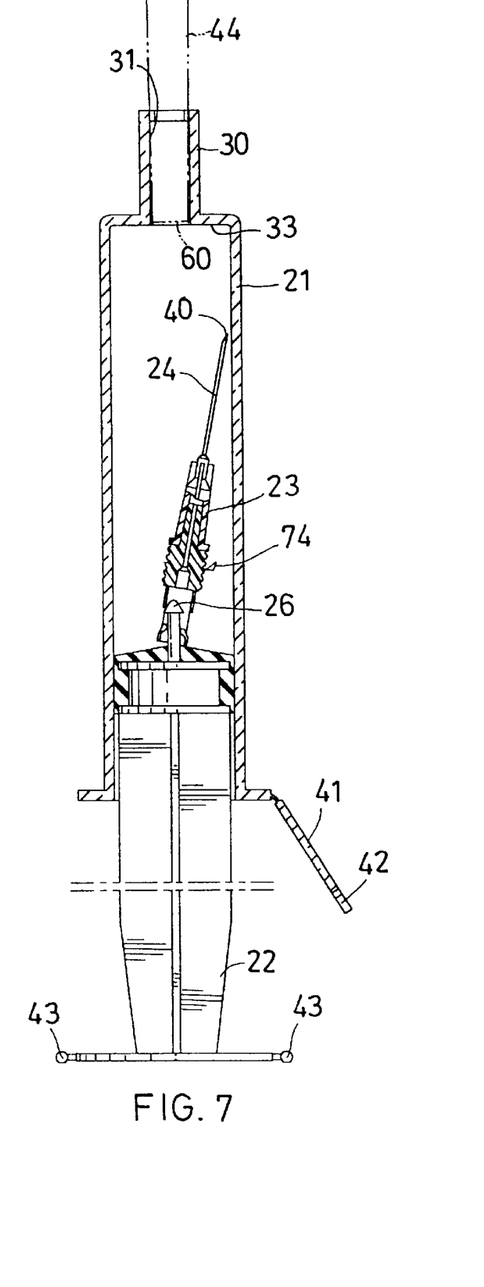
FIG. 7 is a longitudinally sectional view according to FIG. 6, showing that the injection needle, first needle holder and second needle holder are together pulled into the barrel and tilted laterally to inner wall of the barrel.

As shown in FIG. 7, after the injection needle 24 is totally pulled back into the barrel 21, the detent 26 is loosely fitted with the clicks 25, 25'. Therefore, the tip 40 of the injection needle 24 will be unstably laterally tilted and positioned under the shoulder section 33 of the barrel 21. At this time, as shown by FIG. 7, a tail end 60 of the needle sheath 44 with less diameter is inserted into the needle holder cavity 31 to seal the cavity 31 and prevent the tip 40 from extending out therefrom. With the tip 40 positioned under the shoulder section 33, the injection needle 24 is unable to hurt any one and the safety syringe 20 can be further processed and destroyed.

Figure 12:
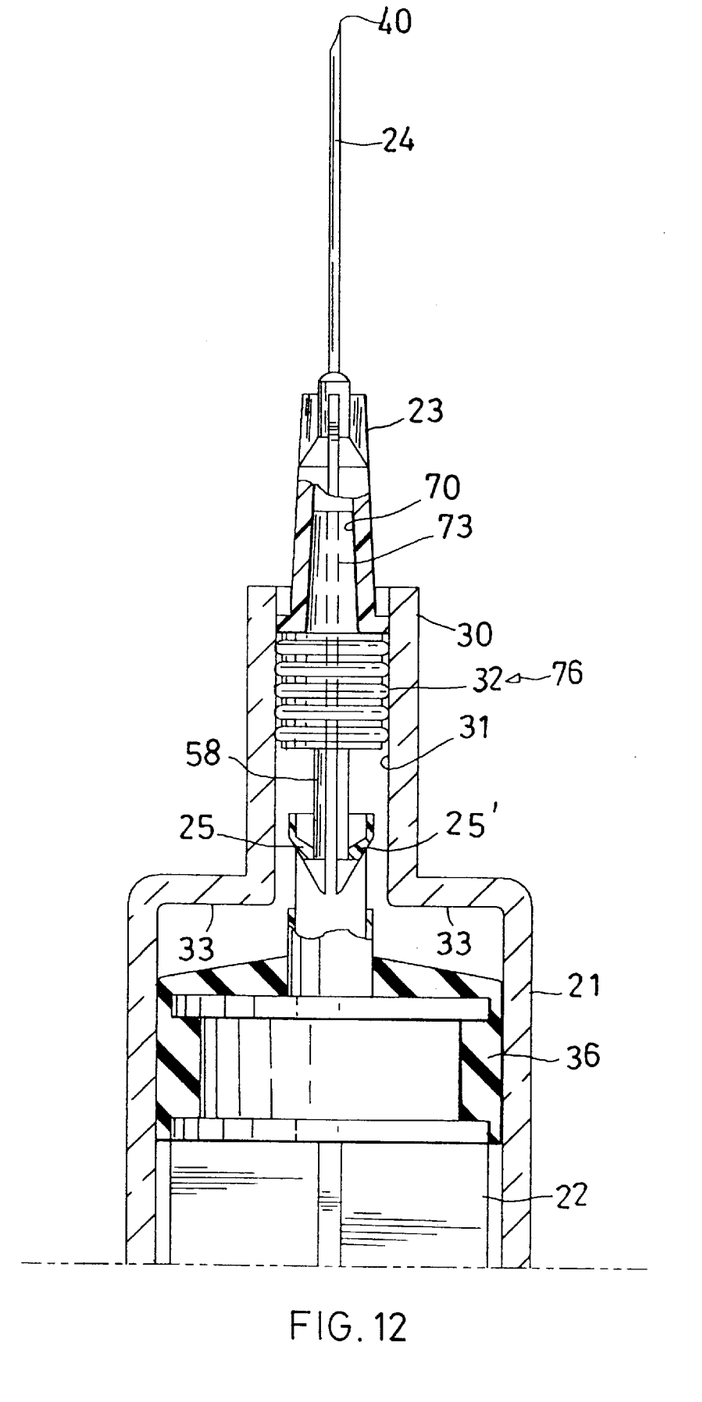
FIG. 12 is a partially sectional view of a fourth embodiment of the present invention.

FIG. 12 shows a fourth embodiment of the present invention, which is identical to the first embodiment shown by FIGS. 1 to 9 except that the positions of the clicks 25, 25' and the detent 26 are exchanged.

According to the above arrangements, the present invention has the following advantages:

1. The safety syringe employs common standard needle holder, permitting a user to conveniently replace the injection needle with another type of injection needle as necessary.
2. The leakproof mechanism is able to avoid leakage of liquid medicine. Also, the safety syringe prevents the injection needle from unexpectedly detaching from the barrel. In addition, the injection needle can be easily pulled back into the barrel.
3. The safety syringe enables the plunger to easily firmly latch with the injection needle so as to reliably pull the injection needle into the barrel.
4. The safety syringe can avoid mis-latching of the injection needle prior to injection.

It is to be understood that the above description and drawings are only used for illustrating some embodiments of the present invention, not intended to limit the scope thereof. Any variation and derivation from the above description and drawings should be included in the scope of the present invention.

What is claimed is:

1. A safety syringe with retratable standard needle, comprising:

(A) a syringe barrel having a first end and a second end, the syringe barrel being formed with an internal barrel chamber, the first end of the barrel being disposed with a needle socket defining a needle holder cavity, an annular shoulder section being formed between the barrel chamber and the needle holder cavity;

(B) a plunger having a first and a second ends, the first end being disposed with a piston and fitted into the barrel, the plunger having a first axis;

(C) a first needle holder having a first and a second ends, the second end of the first needle holder having a first fitting section;

(D) an injection needle inserted into the first end of the first needle holder;

(E) a second needle holder having a first end, a second end, a second fitting section and a plug section, the second fitting section being disposed at the first end and detachably connected with the first fitting section of the first needle holder, the plug section being disposed at the second end and fitted in the needle holder cavity of the needle socket, the second needle holder having a second axis, the second needle holder being formed with a through hole coaxial with the second axis for guiding a liquid medicine to flow through the through hole toward the injection needle or flow from the injection needle through the through hole into the barrel; and (F) a needle pulling mechanism including:

(a) a first needle pulling member having a first end and a second end, the first end being integrally connected with one of the first end of the plunger and the second end of the second needle holder, the first needle pulling member having at least one click each having a first end and a second end, the first end being rotatably connected with the second end of the first needle pulling member, a distance between the first end of the click and either of the first axis and second axis being defined as a first distance, the second end of the click extending to the first end of the first needle pulling member, a distance between the second end of the click in a free state and either of the first axis and second axis being defined as a second distance which is less than the first distance, a distance between the second end of the click and the first end of the first needle pulling member being defined as a third distance, a distance between the first end of the click and the first end of the first needle pulling member being defined as a fourth distance which is larger than the third distance, whereby the click is formed as a ratchet; and (b) a second needle pulling member having a first end and a second ends, the first end being connected with the other of the first end of the plunger and the second end of the second needle holder, the first end of the second needle pulling member being formed as a stem and the second end of the second needle pulling member being formed as a detent having a hook section, the hook section being formed with a radially extending hook face, when the first end of the plunger is pushed to the first end of the barrel, the hook section of the detent stretching open and sliding over the second end of the click, when the plunger is pulled from the first end of the barrel to the second end thereof, the hook face of the hook section of the detent abutting against the second end of the click with the stem tightly clamped by the second end of the click, whereby the first needle holder, the second needle holder and the injection needle can be together pulled into the barrel.

2. A safety syringe as claimed in claim 1, further comprising at least two radially arranged clicks.

3. A safety syringe as claimed in claim 1, wherein the first needle holder is a commonly used standard needle holder and the first fitting section thereof is formed with a truncated conic cavity.

4. A safety syringe as claimed in claim 3, wherein the second fitting section is formed as a truncated cone for detachably fitting into the truncated conic cavity of the first fitting section.

5. A safety syringe as claimed in claim 1, further comprising a leakproof structure including at least one sealing ring integrally formed on one of the wall of the needle holder cavity and the outer wall of the plug section of the second needle holder, the sealing ring sealedly contacting with the other of the wall of the needle holder cavity and the outer wall of the plug section of the second needle holder.

6. A safety syringe as claimed in claim 1, further comprising a leakproof structure including at least one first sealing ring and at least one second sealing ring, the first sealing ring being integrally formed on one of the wall of the needle holder cavity and the outer wall of the plug section of the second needle holder, the first sealing ring sealedly contacting with the other of the wall of the needle holder cavity and the outer wall of the plug section of the second needle holder, the second sealing ring being integrally formed on the other of the wall of the needle holder cavity and the outer wall of the plug section of the second needle holder, the second sealing ring sealedly contacting with said one of the wall of the needle holder cavity and the outer wall of the plug section of the second needle holder.

7. A safety syringe as claimed in claim 6, wherein one of the first and second sealing rings is adjacent to the other of the first and second sealing rings.

* * * * *

UNITED STATES PATENT AND TRADEMARK OFFICE
CERTIFICATE OF CORRECTION

PATENT NO. : 5,899,887
DATED : 4 May 1999
INVENTOR(S) : WEN-NENG LIU

It is certified that error appears in the above-identified patent and that said Letters Patent is hereby corrected as shown below:

Title page item [30], delete the number "87105506" and insert therefor the number --87105505--

Signed and Sealed this

Seventeenth Day of October, 2000

Attest:

Q. TODD DICKINSON

*Attesting Officer*   *Director of Patents and Trademarks*